(12) United States Patent
Kawaguchi (10) Patent No.: US 10,383,893 B2
(45) Date of Patent: *Aug. 20, 2019

(54) COMPOSITION FOR REDUCING THE LEVEL OF GLUCOSE, MALONDIALDEHYDE-MODIFIED LDL, HOMOCYSTEINE AND/OR C-REACTIVE PROTEIN IN BLOOD

(75) Inventor: Susumu Kawaguchi, Tokyo (JP)

(73) Assignee: NUTRI CO., LTD., Mie (JP)

( * ) Notice: Subject to any disclaimer, the term of this patent is extended or adjusted under 35 U.S.C. 154(b) by 876 days.

This patent is subject to a terminal disclaimer.

(21) Appl. No.: 12/739,701

(22) PCT Filed: Oct. 23, 2008

(86) PCT No.: PCT/JP2008/069244
§ 371 (c)(1),
(2), (4) Date: Apr. 23, 2010

(87) PCT Pub. No.: WO2009/054458
PCT Pub. Date: Apr. 30, 2009

(65) Prior Publication Data
US 2010/0247505 A1    Sep. 30, 2010

(30) Foreign Application Priority Data

Oct. 25, 2007  (JP) .................. 2007-277140

(51) Int. Cl.
*A61K 31/07*  (2006.01)
*A61K 31/51*  (2006.01)
(Continued)

(52) U.S. Cl.
CPC .............. *A61K 33/30* (2013.01); *A61K 31/07* (2013.01); *A61K 31/197* (2013.01);
(Continued)

(58) Field of Classification Search
CPC .... A61K 31/07; A61K 31/197; A61K 31/355; A61K 31/375; A61K 31/385;
(Continued)

(56) References Cited

U.S. PATENT DOCUMENTS 4,927,850 A    5/1990  Bayless et al.
5,364,644 A *  11/1994 Walaszek et al. ............ 514/574
(Continued)

FOREIGN PATENT DOCUMENTS

CN        1686547         10/2005
DE   202006014588 U1 *  12/2006  ............. A23L 1/302
(Continued)

OTHER PUBLICATIONS

Colagiuri et al. (American Journal of Public Health, Sep. 2006, vol. 96, No. 9, pp. 1562-1569).*
(Continued)

*Primary Examiner* — Kortney L. Klinkel
(74) *Attorney, Agent, or Firm* — Morgan, Lewis & Bockius LLP (57) ABSTRACT

Disclosed is a composition for reducing the levels or level of glucose, malondialdehyde-modified LDL, homocysteine, and/or C-reactive protein in the blood. Specifically disclosed is a composition for reducing the level of at least one substance selected from the group consisting of glucose, malondialdehyde-modified LDL, homocysteine, and C-reactive protein in the blood, which comprises the following components (a) and (b): (a) at least one component selected from the group consisting of vitamin $B_{12}$, vitamin $B_6$, and folic acid; and (b) at least one component selected from the group consisting of zinc, selenium, and an antioxidant vitamin.

21 Claims, 4 Drawing Sheets

(51) Int. Cl.
| | |
|---|---|
| A61K 33/00 | (2006.01) |
| A61K 33/04 | (2006.01) |
| A61K 33/06 | (2006.01) |
| A61K 33/24 | (2019.01) |
| A61K 33/30 | (2006.01) |
| A61K 33/42 | (2006.01) |
| A61K 45/06 | (2006.01) |
| A61K 31/197 | (2006.01) |
| A61K 31/355 | (2006.01) |
| A61K 31/375 | (2006.01) |
| A61K 31/385 | (2006.01) |
| A61K 31/455 | (2006.01) |
| A61K 31/525 | (2006.01) |
| A61K 31/593 | (2006.01) |
| A61K 31/702 | (2006.01) |
| A61K 31/714 | (2006.01) |
| A61K 31/4188 | (2006.01) |
| A61K 31/4415 | (2006.01) |

(52) U.S. Cl.
CPC .......... A61K 31/355 (2013.01); A61K 31/375 (2013.01); A61K 31/385 (2013.01); A61K 31/4188 (2013.01); A61K 31/4415 (2013.01); A61K 31/455 (2013.01); A61K 31/51 (2013.01); A61K 31/525 (2013.01); A61K 31/593 (2013.01); A61K 31/702 (2013.01); A61K 31/714 (2013.01); A61K 33/00 (2013.01); A61K 33/04 (2013.01); A61K 33/06 (2013.01); A61K 33/24 (2013.01); A61K 33/42 (2013.01); A61K 45/06 (2013.01)

(58) Field of Classification Search
CPC ............ A61K 31/4188; A61K 31/4415; A61K 31/455; A61K 31/51; A61K 31/525; A61K 31/593; A61K 31/702; A61K 31/714; A61K 33/04; A23V 2250/706; A23V 2250/7052; A23V 2250/2056; A23V 2250/1642; A23V 2250/1626; A23V 2250/708; A23V 2250/712; A23V 2250/7106; A23V 2250/7042; A23V 2250/72; A23V 2250/7044; A23V 2250/7046; A23V 2250/705

See application file for complete search history.

(56) References Cited

U.S. PATENT DOCUMENTS

| | | | |
|---|---|---|---|
| 5,569,670 A | 10/1996 | Weischer et al. ............. 514/440 |
| 6,261,606 B1 | 7/2001 | Mirsky et al. ................ 424/725 |
| 6,274,170 B1 | 8/2001 | Heibel et al. | |
| 6,361,800 B1 | 3/2002 | Cooper et al. ................ 424/630 |
| 6,515,018 B1 | 2/2003 | Fuhrman et al. ............. 514/458 |
| 7,208,180 B2 | 4/2007 | Kiliaan et al. | |
| 2002/0040058 A1 | 4/2002 | Kiliaan et al. | |
| 2002/0146463 A1* | 10/2002 | Clayton ........................ 424/617 |
| 2004/0052922 A1 | 3/2004 | Pistolesi | |
| 2005/0147665 A1 | 7/2005 | Horrobin et al. ............. 424/456 |
| 2006/0063768 A1 | 3/2006 | Mueller et al. ............... 514/251 |
| 2006/0105033 A1 | 5/2006 | Bendich | |
| 2006/0116334 A1 | 6/2006 | Hendrix | |
| 2008/0102137 A1* | 5/2008 | Guffey .................. A61K 31/355 424/641 |
| 2008/0292724 A1 | 11/2008 | Hageman et al. | |
| 2008/0318883 A1 | 12/2008 | Hatanaka et al. | |
| 2009/0022813 A1 | 1/2009 | Hageman | |
| 2009/0156487 A1 | 6/2009 | Zwijsen et al. | |
| 2009/0220637 A1 | 9/2009 | Roessle | |

FOREIGN PATENT DOCUMENTS

| | | |
|---|---|---|
| JP | 06-192105 | 7/1994 |
| JP | 2002-504928 | 2/2002 |
| JP | 2002-348244 | 12/2002 |
| JP | 2003-504333 | 2/2003 |
| JP | 2003-509389 | 3/2003 |
| JP | 2003-530410 | 10/2003 |
| JP | 2004-217669 | 8/2004 |
| JP | 2005-524655 | 8/2005 |
| JP | 2006-513717 | 4/2006 |
| JP | 2006-306820 | 11/2006 |
| JP | 2007-106703 | 4/2007 |
| WO | 0048578 A1 | 8/2000 |
| WO | 02052955 A1 | 7/2002 |
| WO | 2007042341 A1 | 4/2007 |
| WO | 2007073178 A2 | 6/2007 |

OTHER PUBLICATIONS

Park (Diabetes Research and Clinical Practice, 2004, 66S, S33-S35).*
Curtis et al. (The Journal of the American Board of Family Practice, 2005, vol. 18, pp. 37-43).*
Christie ("What is a Lipid?" AOCS Lipid Library, updated Jul. 25, 2013 accessed via http://lipidlibrary.aocs.org/Primer/content.cfm?ItemNumber=39371 on Nov. 4, 2015).*
Lipid article from Wikipedia accessed via https://en.wikipedia.org/wiki/Lipid on Nov. 4, 2015.*
DE202006014588 machine translation, Dec. 14, 2006, Orthomol Pharmazeutische Vertiebs Gmbh.*
Machine translation of JP2007106703 to Akihiko Nakagawa, accessed via InnovationQ (https://iq/ip.com/discover May 22, 2018).*
Machine translation of JP2007106703 from the EPO, accessed May 22, 2018.*
Extended European search report dated Nov. 16, 2010 for corresponding European application 08841027.9 cites the U.S. Patents, U.S. Patent Application Publications and Foreign Patent Documents above.
International Preliminary Report on Patentability dated Jun. 10, 2010 for corresponding PCT application PCT/JP2008/069244.
Timothy S. Church et al., "Reduction of C-Reactive Protein Levels Through Use of a Multivitamin", The American Journal of Medicine, Dec. 15, 2003, vol. 115, pp. 702-707.
Chinese Journal of Misdiagnostics, Mar. 2004, vol. 4, No. 3, 367-369.
Office Action for corresponding Chinese patent application No. 200880112375.X.
Chinese language office action dated Oct. 26, 2012 and its English language translation issued in corresponding Chinese application 200880112375.X.

* cited by examiner

COMPOSITION FOR REDUCING THE LEVEL OF GLUCOSE, MALONDIALDEHYDE-MODIFIED LDL, HOMOCYSTEINE AND/OR C-REACTIVE PROTEIN IN BLOOD

CROSS-REFERENCE TO THE RELATED APPLICATIONS

This application is a national stage of international application No. PCT/JP2008/069244, filed on Oct. 23, 2008, and claims the benefit of priority under 35 USC 119 to Japanese Patent Application No. 2007-277140, filed on Oct. 25, 2007, the entire contents of which are incorporated herein by reference.

TECHNICAL FIELD

The present invention relates to a composition for reducing the levels or level of glucose, malondialdehyde-modified LDL (MDA-LDL), homocysteine, and/or C-reactive protein (CRP) in the blood.

BACKGROUND ART

Diseases such as diabetes mellitus, hyperlipidemia, and hypertension are considered to develop due to an external factor such as a genetic factor, stress, and a pathogen in combination with a lifestyle habit such as an inappropriate eating habit, a lack of exercise, smoking, and excessive alcohol consumption, and these diseases are called a lifestyle-related disease (Non-Patent Document 1). The number of people having or highly likely to have a lifestyle-related disease is increasing as a result of a change in lifestyles and an increase in the elderly population, and thus a comprehensive countermeasure against lifestyle-related diseases needs to be implemented. The Ministry of Health, Labour and Welfare of Japan has begun to strengthen their approach to the above issue, proposing "firstly, exercise, secondly, diet, completely quit smoking, then a medicine comes last" as a catchphrase with the aim of improving lifestyles (Non-Patent Document 2). As exercise therapy for a lifestyle-related disease, an effect of aerobic exercise becomes a focus of attention in sports facilities such as a fitness club, where the number of people who adopt walking, swimming, and the like as an exercise routine is increasing. Also, it is said that a considerable effect on prophylaxis or amelioration of a lifestyle-related disease might be attained through, in addition to exercise guidance, nutritional management in cooperation with a national registered dietitian.

A lifestyle-related disease is defined as "a group of diseases whose development and progress are associated with lifestyle such as an eating habit, an exercise habit, respite, smoking, and alcohol consumption", and representative diseases include dental caries, periodontal disease, osteoporosis, alcoholic liver disease, obesity, gout (hyperuricemia), hypertension, diabetes mellitus, hyperlipidemia, heart disease, cerebral apoplexy, and cancer. "Arteriosclerosis" is known as a pathological condition associated with a lifestyle-related disease.

It is postulated that persistent high postprandial glucose levels induce an oxidative stress along with increased glycated protein and activated protein kinase C, and the oxidative stress thus induced causes vascular disorder.

The oxidative stress is considered to cause activation of blood vessel-constituting cells and blood cells such as monocytes and platelets and increase secretion of inflammatory cytokines and oxidized LDL (MDA-LDL), resulting in progression and aggravation of vascular disorder. Due to inflammation developed in the above process, the level of CRP, which is an inflammatory marker, also increases. It is considered that the above-described series of reactions lead to development and progression of arteriosclerosis (Non-Patent Document 3).

Homocysteine is an amino acid present in the blood. Homocysteine has become a focus of attention in recent years for its association with arteriosclerosis. It is considered that, in atherosclerosis, monocytes adhere to and infiltrate arterial endothelial cells in response to chemotactic factors secreted due to an endothelial cell injury, and monocytes differentiate into macrophages in intimae. Then, while they take up cholesterol in the blood to cause intimal hyperplasia, they break down to develop an atheromatous condition. It is considered that when homocysteine is accumulated in the blood, it causes autoxidation, and a substance such as radical oxygen produced during the oxidation process damages endothelial cells, increasing the likelihood of arteriosclerosis development (Non-Patent Document 4). Arteriosclerosis is also known as a complication of diabetes mellitus, and it is considered that arteriosclerosis and diabetes mellitus are closely associated.

Non-Patent Document 1: Prophylaxis of lifestyle-related disease and exercise and nutritional management, ISHII, Keiko et al., the Japanese Journal of Clinical Nutrition, Vol. 108, No. 2, February 2006

Non-Patent Document 2: Psychosomatic medical approach to lifestyle-related disease, YAMANAKA, Takao et al., Japanese Society of Psychosomatic Medicine, Vol. 46, No. 4, April 2006

Non-Patent Document 3: Journal of Clinical and Experimental Medicine, Vol. 218, No. 1, July $1^{st}$, 2006, YAMAGISHI, Shoichi Non-Patent Document 4: Journal of Clinical and Experimental Medicine, 202(10): 789-793, 2002

DISCLOSURE OF THE INVENTION

Problems to be Solved by the Invention

An object of the present invention is to provide a composition for reducing the levels or level of glucose, malondialdehyde-modified LDL, homocysteine, and/or C-reactive protein in the blood.

Means for Solving the Problems

The present inventor asked people having or highly likely to have a lifestyle-related disease to consume a composition containing the following components (a) and (b) in order to verify the usefulness of the composition. As a result, they have found that the composition is effective for reducing the levels or level of glucose, malondialdehyde-modified LDL, homocysteine, and/or C-reactive protein in the blood, thereby completing the present invention:

(a) at least one component selected from the group consisting of vitamin $B_{12}$, vitamin $B_6$, and folic acid; and
(b) at least one component selected from the group consisting of zinc, selenium, and an antioxidant vitamin.

The present invention is summarized as follows.
(1) A composition for reducing the level of at least one substance selected from the group consisting of glucose, malondialdehyde-modified LDL, homocysteine, and C-reactive protein in the blood, comprising the following components (a) and (b):

(a) at least one component selected from the group consisting of vitamin $B_{12}$, vitamin $B_6$, and folic acid; and
(b) at least one component selected from the group consisting of zinc, selenium, and an antioxidant vitamin.
(2) The composition according to the above (1), further comprising α-lipoic acid and/or chromium.
(3) The composition according to the above (2) comprising vitamin $B_{12}$, vitamin $B_6$, folic acid, zinc, selenium, vitamin C, vitamin E, α-lipoic acid, chromium, vitamin $B_2$, vitamin $B_1$, niacin, pantothenic acid, vitamin A, vitamin $D_3$, and biotin.
(4) The composition according to the above (3) comprising, per dosage unit, 10±2 μg of vitamin $B_{12}$, 5±1 mg of vitamin $B_6$, 800±160 μg of folic acid, 10±2 mg of zinc, 50±10 us of selenium, 500±100 mg of vitamin C, 20±4 mg of vitamin E, 30±6 mg of α-lipoic acid, 30±6 μg of chromium, 3±0.6 mg of vitamin $B_2$, 3±0.6 mg of vitamin $B_1$, 15±3 mg of niacin, 10±2 mg of pantothenic acid, 300±60 μg of vitamin A (retinal equivalent), 5±1 μg of vitamin $D_3$, and 50±10 μg of biotin, and having an energy of 46±9.2 kcal.
(5) The composition according to any one of the above (1) to (4), further comprising galacto-oligosaccharide, potassium, calcium, magnesium, and phosphorus.
(6) The composition according to the above (5) comprising, per dosage unit, 2±0.4 g of galacto-oligosaccharide, 40±8 mg of potassium, 80±16 mg of calcium, 3±0.6 mg of magnesium, and 7.5±1.5 mg of phosphorus.
(7) The composition according to any one of the above (1) to (6), which is dispersed in a liquid that can be dosed.
(8) The composition according to the above (7), which has a volume of 125±25 mL per dosage unit.
(9) The composition according to any one of the above (1) to (8), which is to be used for treatment and/or prophylaxis of a lifestyle-related disease.
(10) The composition according to the above (9), wherein the lifestyle-related disease is diabetes mellitus, arteriosclerosis, or metabolic syndrome.
(11) The composition according to any one of the above (1) to (10), which is to be administered to a person having or highly likely to have a lifestyle-related disease.
(12) A method for reducing the level of at least one substance selected from the group consisting of glucose, malondialdehyde-modified LDL, homocysteine, and C-reactive protein in the blood, including administering to a subject effective amounts of the following components (a) and (b) for reducing the level of at least one substance selected from the group consisting of glucose, malondialdehyde-modified LDL, homocysteine, and C-reactive protein in the blood:
(a) at least one component selected from the group consisting of vitamin $B_{12}$, vitamin $B_6$, and folic acid; and
(b) at least one component selected from the group consisting of zinc, selenium, and an antioxidant vitamin.
(13) A method of treatment and/or prophylaxis of a lifestyle-related disease comprising administering to a subject effective amounts of the following components (a) and (b) for treatment and/or prophylaxis of the lifestyle-related disease:
(a) at least one component selected from the group consisting of vitamin $B_{12}$, vitamin $B_6$, and folic acid; and
(b) at least one component selected from the group consisting of zinc, selenium, and an antioxidant vitamin.
(14) The method according to the above (13), wherein the lifestyle-related disease is diabetes mellitus, arteriosclerosis, or metabolic syndrome.
(15) Use of the following components (a) and (b) for production of a composition for reducing the level of at least one substance selected from the group consisting of glucose, malondialdehyde-modified LDL, homocysteine, and C-reactive protein in the blood:
(a) at least one component selected from the group consisting of vitamin $B_{12}$, vitamin $B_6$, and folic acid; and
(b) at least one component selected from the group consisting of zinc, selenium, and an antioxidant vitamin.
(16) Use of the following components (a) and (b) for production of a composition for treatment and/or prophylaxis of a lifestyle-related disease:
(a) at least one component selected from the group consisting of vitamin $B_{12}$, vitamin $B_6$, and folic acid; and
(b) at least one component selected from the group consisting of zinc, selenium, and an antioxidant vitamin.
(17) The use according to the above (16), wherein the lifestyle-related disease is diabetes mellitus, arteriosclerosis, or metabolic syndrome.

Advantage of the Invention

A composition for reducing the levels or level of glucose, malondialdehyde-modified LDL, homocysteine, and/or C-reactive protein in the blood was provided according to the present invention.

The present specification encompasses the description set forth in the specification and/or drawings of Japanese Patent Application No. 2007-277140, based on which the present application claims priority.

BEST MODE FOR CARRYING OUT THE INVENTION

Hereinafter, embodiments of the present invention will be described in more detail.

The present invention provides a composition for reducing the level of at least one substance selected from the group consisting of glucose, malondialdehyde-modified LDL, homocysteine, and C-reactive protein in the blood, comprising the following components (a) and (b):
(a) at least one component selected from the group consisting of vitamin $B_{12}$, vitamin $B_6$, and folic acid; and
(b) at least one component selected from the group consisting of zinc, selenium, and an antioxidant vitamin.

Vitamin $B_{12}$, vitamin $B_6$, and folic acid are components that are involved in homocysteine metabolism. These components involved in the homocysteine metabolism activate a metabolic process that converts methionine to cysteine, so they are considered to contribute to a reduction in the blood homocysteine level. While the composition of the present invention can also contain any of vitamin $B_6$, vitamin $B_{12}$, and folic acid alone, it preferably contains a plurality of the above three components in combination, and most preferably contains all of the above three components in combination.

The composition of the present invention contains, for example, 1.1 µg to 50.0 µg, preferably 5.0 µg to 15.0 µg of vitamin $B_{12}$, 1.6 mg to 60.0 mg, preferably 3.0 mg to 8.0 mg of vitamin $B_6$, and 200 µg to 1.1 mg, preferably 600 µg to 1,000 µg of folic acid, per dosage unit.

Zinc, selenium, and an antioxidant vitamin are a group of components that are involved in removal of active oxygen. Active oxygen is considered to be involved in vascular endothelial dysfunction, and therefore, the above-described components involved in removal of active oxygen play an important role in ameliorating vascular endothelial dysfunction. Selenium is a constitutive substance of glutathione peroxidase which is an antioxidant enzyme, and zinc is a constitutive substance of superoxide dismutase which is another antioxidant enzyme. Antioxidant vitamins such as vitamin E and vitamin C can exist in a reduced form or an oxidized form, and they oxidize themselves by accepting free radicals from active oxygen, thereby functioning to remove active oxygen. While the composition of the present invention can also contain any of zinc, selenium, and an antioxidant vitamin alone, it preferably contains a plurality of the above components in combination. Examples of the antioxidant vitamin include, but are not limited to, vitamin C, vitamin E, and vitamin A. The intake amount of vitamins varies depending on the diet, and particularly, patients having diabetes mellitus or highly likely to have diabetes mellitus who require dietary restriction tend to be deficient in vitamin intake. In view of the above, it is desirable that the composition of the present invention contain a plurality of antioxidant vitamins in combination.

The composition of the present invention contains, for example, 1.2 mg to 30 mg, preferably 9 mg to 12 mg of zinc, and 10 µg to 250 µg, preferably 30 µg to 60 µg of selenium, per dosage unit. Further, when vitamin C, vitamin E, or vitamin A is employed as an antioxidant vitamin, the composition of the present invention contains, for example, 100 mg to 2000 mg, preferably 300 mg to 1000 mg of vitamin C, 3 mg to 600 mg, preferably 5 mg to 300 mg of vitamin E, and 10 µg to 3,000 µg, preferably 100 µg to 550 µg of vitamin A (retinol equivalent), per dosage unit.

The composition of the present invention may further contain α-lipoic acid and/or chromium. The α-lipoic acid is involved in promotion of glucose metabolism. It is considered that α-lipoic acid stimulates mobilization of an intracellular glucose transporter (GLUT-4) to a cellular membrane, whereby the amount of glucose uptake mediated by insulin in muscle and a myocyte is considerably increased.

The content of α-lipoic acid is, for example, appropriately 20 mg to 1,000 mg, preferably 25 mg to 100 mg, per dosage unit.

Chromium increases insulin sensitivity by enhancing the binding capacity of insulin receptor, increasing the number of insulin receptors, and enhancing the activity of an insulin receptor kinase.

The content of chromium is, for example, appropriately 5 µg to 50 µg, preferably 10 µg to 40 mg per dosage unit.

The composition of the present invention may further contain other components besides the above-described components. For example, the composition of the present invention may contain calcium which is prone to be deficient in a normal diet as described above, as well as vitamin D which promotes calcium absorption (for example, vitamin $D_3$), and the like. Also, vitamins other than the ones exemplified above as vitamins involved in homocysteine metabolism and as antioxidant vitamins (for example, vitamin $B_2$, vitamin $B_1$, niacin, and pantothenic acid) may be exemplified as components to be favorably contained in the composition of the present invention. The composition of the present invention may also contain biotin, galacto-oligosaccharide, potassium, magnesium, and phosphorus. Deficiency of components in restricted diets such as a diabetic diet can be prevented by including the above-described components in the composition of the present invention. Further, β-carotene, iron, coenzyme Q10, and the like can be added to the composition of the present invention. The β-carotene is a precursor of vitamin A. It is absorbed from the gastrointestinal tract, and only a necessary amount of β-carotene is converted to vitamin A. Thus, there is no concern for an excessive intake of vitamin A. In terms of action, β-carotene functions in a similar way to vitamin A. Because iron is a constitutive component of hemoglobin, there is a risk for the development of anemia if iron is deficient. Prophylactic, preventive, and improving effects on an anemic symptom are anticipated with incorporation of iron. As coenzyme Q10 has a strong antioxidative action, it is anticipated to exhibit prophylactic and preventive effects on diseases attributable to oxidative stress. Also, because coenzyme Q10 is a component involved in ATP production, a beneficial effect such as smooth metabolism of nutrients is anticipated by supplementation with coenzyme Q10.

The composition of the present invention contains, for example, appropriately 0.5 mg to 20 mg, preferably 1 mg to 10 mg of vitamin $B_2$, appropriately 0.5 mg to 10 mg, preferably 1.0 mg to 5.0 mg of vitamin $B_1$, appropriately 1 mg to 100 mg, preferably 5 mg to 50 mg of niacin, appropriately 1 mg to 100 mg, preferably 5 mg to 50 mg of pantothenic acid, appropriately 1 µg to 10 µg, preferably 2 mg to 8 µg of vitamin $D_3$, appropriately 1 µg to 200 µg, preferably 10 µg to 100 µg of biotin, appropriately 0.1 mg to 100 mg, preferably 1.0 mg to 50 mg of β-carotene, appropriately 0.5 mg to 50 mg, preferably 1.0 mg to 30 mg of iron, and appropriately 1.0 mg to 1,000 mg, preferably 2 mg to 100 mg of coenzyme Q10, per dosage unit.

Further, the composition of the present invention contains, for example, appropriately 0.1 g to 20 g, preferably 1 g to 10 g of galacto-oligosaccharide, appropriately 10 mg to 1,000 mg, preferably 15 mg to 500 mg of potassium, appropriately 1 mg to 2,300 mg, preferably 10 mg to 600 mg of calcium, 0.1 mg to 10 mg, preferably 1 mg to 5 mg of magnesium, and appropriately 1 mg to 3500 mg, preferably 5 mg to 1050 mg of phosphorus, per dosage unit.

The amount of energy in the composition of the present invention is appropriately 5 kcal to 200 kcal, preferably 20 kcal- to 150 kcal, per dosage unit. Also, with regard to general components, the content of protein, for example, may be approximately 0.4±10.08 g or approximately 0.7±0.14 g, the content of carbohydrate may be approximately 11.1±2.22 g or approximately 21.2±4.24 g, and the content of sodium may be approximately 30±6 mg, per dosage unit.

The composition of the present invention may be prepared in accordance with methods well known to a person skilled in the art. For example, the above-described components may be mixed and prepared into such dosage forms as powder, granule, tablet, and liquid. A liquid is a preferable dosage form because it can be administered through a tube to a patient having a difficulty with oral intake.

When the composition of the present invention is prepared as a liquid, there is no limitation on liquids in which the composition is dispersed or dissolved as long as they are liquids that are commonly administered and they do not reduce the action to be exerted on a living body by each component. For example, water and physiological saline can be used. In oral administration, fruit juice may be used to improve taste. The fruit juice may be blueberry juice, grape juice, grapefruit juice, lemon juice, orange juice, carrot juice, apple juice, and pineapple juice. Among them, blueberry juice and grape juice are preferable considering that the sourness and smell of vitamin C and a group of vitamin B's can be relieved. In the case of a liquid, the volume is appropriately 10 ml to 250 ml, preferably 50 ml to 200 ml, and more preferably 125±25 ml, per dosage unit. Also, in the case of a liquid, the water content may be, for example, approximately 116±23.2 g or 110±22 g, per dosage unit.

The following Table 1 is an example of a table of components for the composition of the present invention (in 125 mL).

TABLE 1

| | | Composition A | Composition B |
|---|---|---|---|
| Energy | | 80 ± 16 kcal | 46 ± 9.2 kcal |
| General components | Protein | 0.7 ± 0.14 g | 0.4 ± 0.08 g |
| | Lipid | 0 g | 0 g |
| | Carbohydrate | 21.2 ± 4.24 g | 11.1 ± 2.22 g |
| | Sodium | 30 ± 6 mg | 30 ± 6 mg |
| Minerals | Potassium | 90 ± 18 mg | 40 ± 8 mg |
| | Calcium | 70 ± 14 mg | 80 ± 16 mg |
| | Magnesium | 3 ± 0.6 mg | 3 ± 0.6 mg |
| | Phosphorus | 30 ± 6 mg | 7.5 ± 1.5 mg |
| Trace elements | Iron | 5 ± 1 mg | 0 mg |
| | Zinc | 10 ± 2 mg | 10 ± 2 mg |
| | Copper | 0.01 ± 0.002 mg | 0 mg |
| | Selenium | 50 ± 10 μg | 50 ± 10 μg |
| | Chromium | — | 30 ± 6 μg |
| Vitamins | Vitamin A (retinol equivalent) | — | 300 μg ± 60 μg |
| | β-carotene | 6.6 ± 1.32 mg | — |
| | Vitamin $B_1$ | 3 ± 0.6 mg | 3 ± 0.6 mg |
| | Vitamin $B_2$ | 3 ± 0.6 mg | 3 ± 0.6 mg |
| | Vitamin $B_6$ | 5 ± 1 mg | 5 ± 1 mg |
| | Vitamin $B_{12}$ | 10 ± 2 μg | 10 ± 2 μg |
| | Vitamin C | 500 ± 100 mg | 500 ± 100 mg |
| | Niacin | 15 ± 3 mg | 15 ± 3 mg |
| | Folic acid | 800 ± 160 μg | 800 ± 160 μg |
| | Vitamin $D_3$ | 3.7 ± 0.74 μg | 5 ± 1 μg |
| | Vitamin E | 20 ± 4 mg | 20 ± 4 mg |
| | Biotin | 50 ± 10 μg | 50 ± 10 μg |
| | Pantothenic acid | 10 ± 2 mg | 10 ± 2 mg |
| Coenzyme Q10 | | 15 ± 3 mg | — |
| α-lipoic acid | | — | 30 ± 6 mg |
| Galacto-oligosaccharide | | 2 ± 0.4 g | 2 ± 0.4 g |
| Water | | 110 ± 22 g | 116 ± 23.2 g |

The reducing effect of the composition prepared as above on the level(s) of glucose, malondialdehyde-modified LDL, total homocysteine, and/or C-reactive protein in the blood can be confirmed by administering the composition to a person having or highly likely to have a lifestyle-related disease (for example, diabetes mellitus, arteriosclerosis, and metabolic syndrome) or to an animal model of lifestyle-related disease, collecting the blood before and after administration to measure the level(s) of glucose (for example, the fasting blood glucose level), malondialdehyde-modified LDL, total homocysteine, and/or C-reactive protein in the blood, and then observing the differences between the values measured before and after administration. Alternatively, values measured in a group to which the composition is administered and values measured in a group to which a placebo (for example, a commercially available drink) is administered (control group) may be compared.

The glucose level in the blood can be measured by an enzyme method. That is, glucose is converted into D-glucose-δ-lactone using glucose dehydrogenase (GDH) and a change as expressed by NAD+(P)→NAD(P)H is measured at 340 nm.

The malondialdehyde-modified LDL level in the blood can be measured by a sandwich ELISA method using a malondialdehyde-modified LDL monoclonal antibody and an anti-apo B monoclonal antibody.

The total homocysteine level in the blood can be quantitated by high performance liquid chromatography (HPLC).

The C-reactive protein level in the blood can be measured by latex immuno-nephelometry. That is, a latex particle to which an anti-CRP antibody is adsorbed is reacted with a sample to cause an agglutination reaction through an antigen-antibody reaction, and then a change in absorbance is measured at 572 nm.

Because glucose, malondialdehyde-modified LDL, total homocysteine, and C-reactive protein are involved in lifestyle-related disease as described above, the levels of glucose, malondialdehyde-modified LDL, total homocysteine, and C-reactive protein in the blood can be an index of a therapeutic and/or prophylactic effect on lifestyle-related disease. For example, provided that a normal fasting blood glucose level is 70 mg/dl to 109 mg/di, if the fasting blood glucose level of a subject exceeds 110 mg/dl, other tests such as ones of measuring postprandial glucose levels, 75-g, 2-hour OGTT values, and glycated protein are additionally performed to determine if the subject is a diabetic patient. Also, it has been reported that a referential normal malondialdehyde-modified LDL level is 58.8±17.9 U/L, and that patients with coronary artery disease exhibited higher levels (113.4±49.1 U/L) than patients in a control group (85.2±22.5 U/L) (Reference 1). Also, it has been reported that a normal total homocysteine level is 3.7 nmol/ml to 13.5 nmol/ml, and that the mortality rate due to coronary artery disease is high in patients having a total plasma homocysteine level equal to or higher than 15 nmol/ml, as compared to patients having a total plasma homocysteine level of less than 15 nmol/ml (Reference 2). A normal C-reactive protein level, based on which the presence or absence of an infection is determined, is equal to or less than 0.30 mg/dl. CRP is normally used as an index of inflammation such as an infection. In recent years, high-sensitivity CRP has been developed as an index of chronic atherosclerotic disease, and a level of 0.1 mg/dl is set as a cut-off level of coronary artery disease (Reference 3).

Reference 1: "Development and clinical evaluation of MDA-LDL measurement system", the 13th meeting of the Society of Analytical Bio-Science, SANEKATA, Kazuhiro et al.

Reference 2: "Plasma homocysteine levels and mortality in patients with coronary artery disease", N Engl J Med, Vol. 337, No. 4, pp. 230-6, 1997, Nygard O et.

Reference 3: "High sensitive C-reactive protein: hs-CRP", Thrombosis and Circulation, Vol. 12, No. 4, 2004, TAKAHASHI, Hakuo Accordingly, the composition of the present invention can be used for treatment and/or prophylaxis of lifestyle-related disease. The composition of the present invention may be administered to a person having or highly likely to have a lifestyle-related disease. The composition of the present invention may be administered to a person having or highly likely to have a lifestyle-related disease in a dose of one dosage unit per day. The composition of the present invention may be administered orally or through a tube.

EXAMPLES

Hereinafter, the present invention is specifically described with reference to Examples. It is to be noted that the Examples are provided to describe the present invention, not to limit the scope of the present invention.

[Preparation Example 1] Preparation of the Composition

A composition containing various kinds of components in a fruit juice liquid containing a blueberry extract was prepared. One bottle of the composition (125 ml) contains 300 μg of vitamin A, 3.0 mg of vitamin $B_1$, 3.0 nag of vitamin $B_2$, 5.0 mg of vitamin $B_6$, 10 μg of vitamin $B_{12}$, 500 mg of vitamin C, 15 mg of niacin, 800 μg of folic acid, 5.0 μg of vitamin $D_3$, 20 mg of vitamin E, 50 μg of biotin, 10 mg of pantothenic acid, 10 mg of zinc, 80 mg of calcium, 7.5 mg of phosphorus, 30 mg of sodium, 40 mg of potassium, 50 μg of selenium, 30 μg of chromium, 30 mg of α-lipoic acid, and 2 g of galacto-oligosaccharide.

[Example 1] Usefulness of the Composition

Objective: To request patients on exercise therapy who had or who were highly likely to have a lifestyle-related disease that they consume the composition to verify the usefulness of the composition prepared in Preparation Example 1.

Patients to be treated: Patients having or highly likely to have a lifestyle-related disease who were visiting a hospital as outpatients in Ibaraki Prefecture and receiving an exercise therapy (irrespective of age and sex but limited to patients without gastrointestinal obstruction). In conducting the present study, the patients were fully informed of the contents of the study, and their written consent to the study was voluntarily obtained.

Study method: The patients from whom consent was obtained were requested to drink one bottle of the composition prepared in Preparation Example 1 (125 mL/bottle) per day, and their blood was collected at baseline, after one month, after two months, and after three months. Evaluation items included, besides physical measurement of the body before and after administration, blood pressure, blood biochemical examination, nutritional index, the amount of active oxygen produced, maximal oxygen uptake, the degree of arteriosclerosis (CAVI), general urinalysis, and subjective symptoms. The patients took medicines as usual during the study period but were requested to avoid use of supplement products containing large amounts of vitamins and trace elements. It is to be noted that no restriction was imposed on meal consumption.

Grouping: The patients were randomly assigned to either of two groups, namely a group in which the composition prepared in Preparation Example 1 was to be consumed (an administration group) or a group in which the composition was not to be consumed (a non-administration group), by the "envelope method." The patients in the non-consumption group consumed 125 nil of a control, 46 kcal blueberry juice free of vitamins and trace nutrients (an in-house product: manufactured for controlled trial).

Evaluation items before and after administration:
1) Hematological Examination

Albumin, erythrocyte count, hemoglobin, hematocrit, leukocyte, lymphocyte, platelet count, total protein, fasting blood glucose level, HbAlc, total cholesterol, HDL cholesterol, LDL cholesterol, triglyceride, total bilirubin, direct bilirubin, AST, ALT, γ-GTP, Al-P, LDH, cholinesterase, BUN, creatinine, uric acid, Na, K, Ca, Cl, CRP, adiponectin, ADMA, oxidized LDL, and total homocysteine 2) Special Tests The amount of active oxygen produced, maximal oxygen uptake, and the degree of arteriosclerosis (CAVI)

3) General Urinalysis

Protein, glucose, and urobilinogen

4) Physical Examination

BMI (body weight and height), body temperature, blood pressure, and pulse

5) Subjective Symptoms

Appetite, abdomen enlarged feeling, vomiting, diarrhea, constipation, and the like Evaluation schedule: Subjective symptoms and composition compliance were checked daily and recorded in a journal Evaluation of items requiring the collection of blood and urine was performed a total of four times, once at baseline, then once every month thereafter. Body weight was measured on the date of blood collection.

Assurance of safety: An investigator carefully ensured the safety of the subjects by conducting necessary and appropriate observation and examination while the subjects participated in the study. Also, in order to objectively evaluate the information on efficacy and safety collected in the present study from ethical and scientific viewpoints, the present study was reviewed by an institutional review board.

The number of cases: Twenty cases in each group (a total of 40 cases)

Test period: From July 2006 to August 2007

Termination criteria:

1) Completion: Study participation was terminated three months after the initiation of the study.

2) Discontinuation: Study participation was discontinued in any of the following cases. Resumption of the participation was left to the discretion of a physician in charge.

(1) In the case when a serious adverse event/adverse reaction developed.

(2) In the case when the patient or the patient's family wished to discontinue the participation in the study.

(3) In any other cases when the physician in charge decided that the participation should be discontinued.

Figure 1:
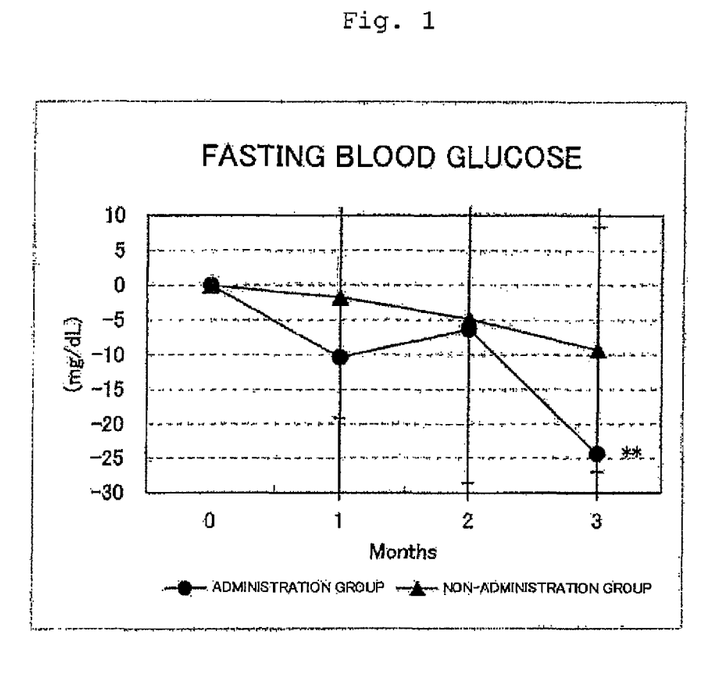
FIG. 1 shows the results for the fasting blood glucose levels. Circles represent the administration group, and triangles represent the non-administration group. Differences from month 0 were averaged out for each group and the values thus obtained were graphed with respect to each group. As a result of a test for significant difference (t-test) from month 0, a value for which a significant difference was observed at $p<0.05$ or $p<0.01$ was indicated by * or **, respectively. In the administration group, a significant decrease ($p<0.01$) was observed at month 3 with respect to month 0.
Figure 2:
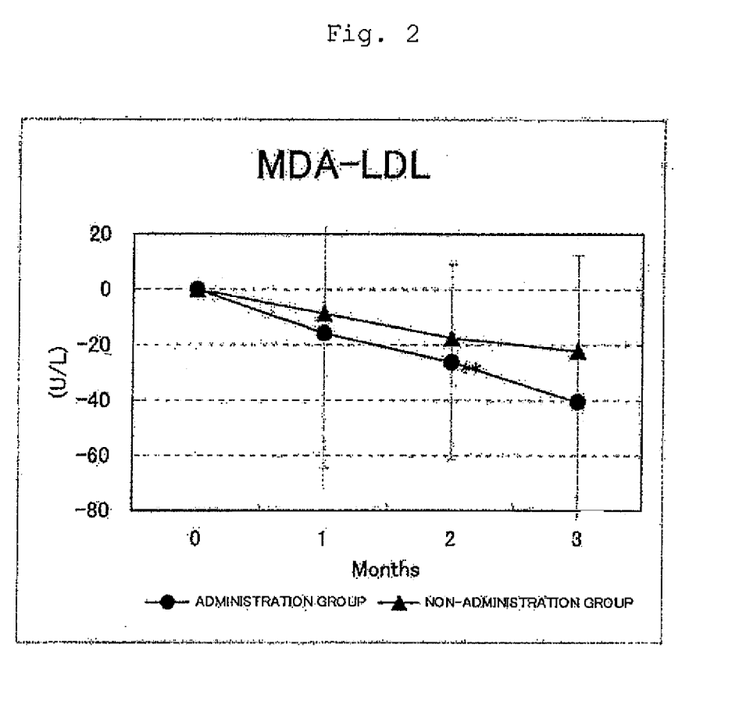
FIG. 2 shows the results for the malondialdehyde-modified LDL levels. Circles represent the administration group, and triangles represent the non-administration group. Differences from month 0 were averaged out for each group and the values thus obtained were graphed with respect to each group. As a result of a test for significant difference (t-test) from month 0, a value for which a significant difference was observed at $p<0.05$ or $p<0.01$ was indicated by * or **, respectively. In the administration group, a significant decrease ($p<0.01$) was observed at month 2 with respect to month 0.
Figure 3:
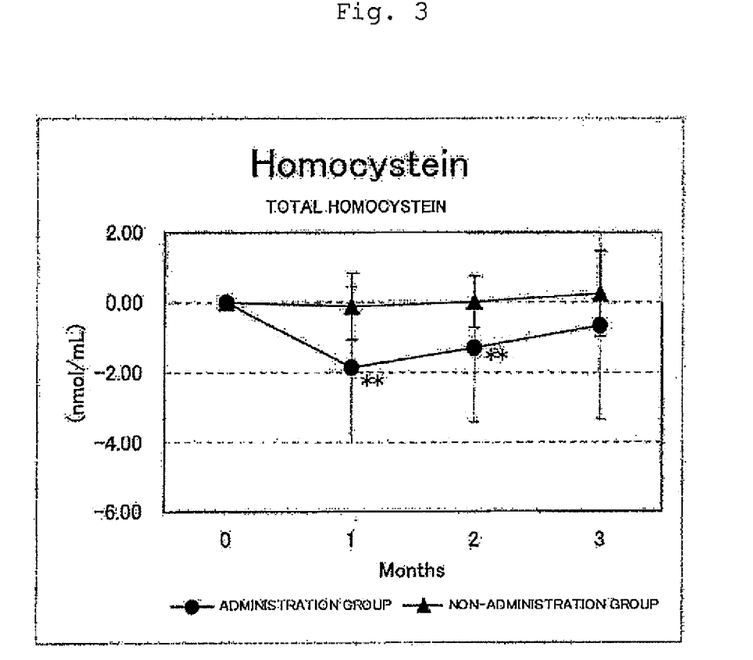
FIG. 3 shows the results for the total homocysteine levels. Circles represent the administration group, and triangles represent the non-administration group. Differences from month 0 were averaged out for each group and the values thus obtained were graphed with respect to each group. As a result of a test for significant difference (t-test) from month 0, a value for which a significant difference was observed at $p<0.05$ or $p<0.01$ was indicated by * or **, respectively. In the administration group, significant decreases ($p<0.01$) were observed at months 2 and 3 with respect to month 0.
Figure 4:
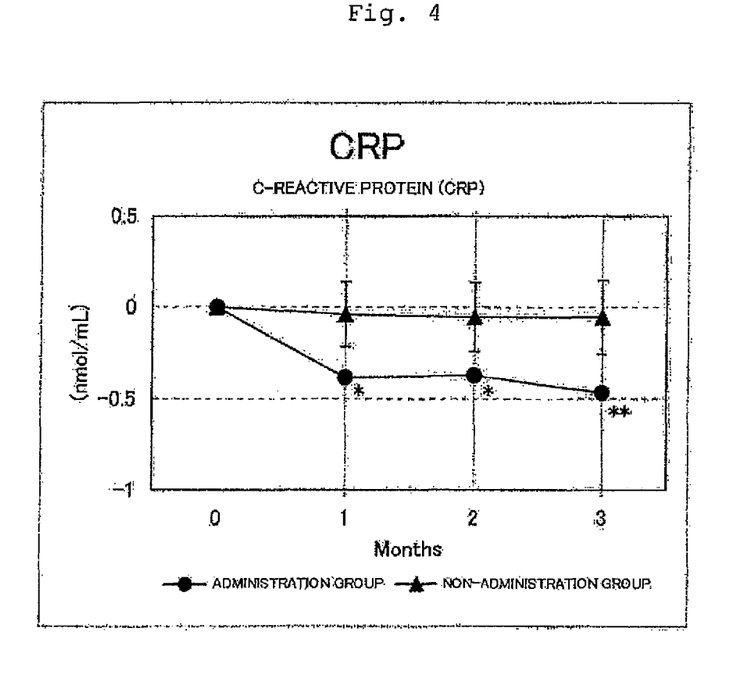
FIG. 4 shows the results for the C-reactive protein (CRP) levels. Circles represent the administration group, and triangles represent the non-administration group. Differences from month 0 were averaged out for each group and the values thus obtained were graphed with respect to each group. As a result of a test for significant difference (t-test) from Month 0, a value for which a significant difference was observed at p<0.05 or p<0.01 was indicated by * or **, respectively. In the administration group, significant decreases (p<0.05) were observed at months 1 and 2, and a significant decrease (p<0.01) was observed at month 3, with respect to month 0.

Results: The results thus obtained are shown in FIGS. 1 to 4. Significant differences were observed with respect to fasting blood glucose level, malondialdehyde-modified LDL, total homocysteine and C-reactive protein (CRP) between the group in which the composition was consumed and the group in which the composition was not consumed.

No significant difference was observed with respect to the evaluation items other than the above items between the group in which the composition was consumed and the group in which the composition was not consumed.)

All the publications, patents and patent applications cited in the present specification are incorporated herein by reference in their entirety.

INDUSTRIAL APPLICABILITY

The composition of the present invention can be used for reducing the levels or level of glucose, malondialdehyde-modified LDL, total homocysteine, and/or C-reactive protein in the blood, and therefore it is useful for treatment and/or prophylaxis of lifestyle-related disease.

The invention claimed is:

1. A method for reducing the levels of glucose, malondialdehyde-modified LDL, homocysteine, and C-reactive protein in the blood of a patient with a disease selected from the group consisting of dental caries, periodontal disease, alcoholic liver disease, obesity, gout, hypertension and cerebral apoplexy, comprising
administering to the patient an effective amount of a composition per dosage unit for reducing the levels of glucose, malondialdehyde-modified LDL, homocysteine, and C-reactive protein in the blood, the composition comprising:
(a) vitamin $B_{12}$ from 1.1 µg to 50.0 µg, vitamin $B_6$ from 1.6 mg to 60.0 mg, and folic acid from 200 µg to 1.1 mg;
(b) zinc from 1.2 mg to 30 mg, selenium from 10 µg to 250 µg vitamin C from 100 mg to 2000 mg, and vitamin E from 3 mg to 600 mg; and
(c) vitamin $D_3$ from 1 µg to 10 µg, vitamin $B_1$ from 1.0 mg to 5.0 mg, biotin from 10 µg to 100 µg, vitamin $B_2$ from 0.5 mg to 20 mg, niacin 1 mg to 100 mg, and pantothenic acid 1 mg to 100 mg,
wherein the composition includes no additional lipid, and the composition further comprises at least two of the following (i)-(iii):
(i) at least one selected from the group consisting of alpha lipoic acid, coenzyme Q10, and blueberry extract,
(ii) at least one selected from magnesium, copper and chromium, and
(iii) galacto-oligosaccharide.

2. The method according to claim 1, wherein the composition is administered orally or through a tube in a dose of one dosage unit per day.

3. The method according to claim 1, wherein the patient is with the disease selected from the group consisting of hypertension, dental caries, and periodontal disease.

4. The method according to claim 1, wherein the composition comprises (i) said at least one selected from the group consisting of alpha lipoic acid, coenzyme Q10, and blueberry extract, and (ii) said at least one selected from magnesium, copper and chromium.

5. The method according to claim 1, wherein the composition comprises (i) said at least one selected from the group consisting of alpha lipoic acid, coenzyme Q10, and blueberry extract, and (iii) said galacto-oligosaccharide.

6. The method according to claim 1, wherein the composition comprises (ii) said at least one selected from magnesium, copper and chromium, and (iii) said galacto-oligosaccharide.

7. A method of producing a composition to be administered to a patient with a disease selected from the group consisting of dental caries, periodontal disease, alcoholic liver disease, obesity, gout, hypertension and cerebral apoplexy for reducing the levels of glucose, malondialdehyde-modified LDL, homocysteine, and C-reactive protein in the blood of the patient, comprising:
incorporating into the composition
(a) vitamin $B_{12}$ from 1.1 µg to 50.0 µg, vitamin $B_6$ from 1.6 mg to 60.0 mg, and folic acid from 200 µg to 1.1 mg;
(b) zinc from 1.2 mg to 30 mg, selenium from 10 µg to 250 µg, vitamin C from 100 mg to 2000 mg, and vitamin E from 3 mg to 600 mg; and
(c) vitamin $D_3$ from 1 µg to 10 µg, vitamin $B_1$ from 1.0 mg to 5.0 mg, biotin from 10 µg to 100 µg, vitamin $B_2$ from 0.5 mg to 20 mg, niacin 1 mg to 100 mg, and pantothenic acid 1 mg to 100 mg,
wherein no additional lipid is incorporated into the composition, and
the composition further comprises at least two of the following (i)-(iii):
(i) at least one selected from the group consisting of alpha lipoic acid, coenzyme Q10, and blueberry extract,
(ii) at least one selected from magnesium, copper and chromium, and
(iii) galacto-oligosaccharide.

8. The method according to claim 7, wherein the composition is to be administered orally or through a tube in a dose of one dosage unit per day.

9. The method according to claim 7, wherein the patient is with the disease selected from the group consisting of hypertension, dental caries, and periodontal disease.

10. A method of treating a patient with a disease selected from the group consisting of dental caries, periodontal disease, alcoholic liver disease, obesity, gout, hypertension and cerebral apoplexy, comprising
administering to the patient an effective amount of a composition per dosage unit for reducing the levels of glucose, malondialdehyde-modified LDL, homocysteine, and C-reactive protein in the blood, the composition comprising:
(a) vitamin $B_{12}$ from 1.1 µg to 50.0 µg, vitamin $B_6$ from 1.6 mg to 60.0 mg, and folic acid from 200 µg to 1.1 mg;
(b) zinc from 1.2 mg to 30 mg, selenium from 10 µg to 250 µg vitamin C from 100 mg to 2000 mg, and vitamin E from 3 mg to 600 mg; and (c) vitamin $D_3$ from 1 μg to 10 μg, vitamin $B_1$ from 1.0 mg to 5.0 mg, biotin from 10 μg to 100 μg, vitamin $B_2$ from 0.5 mg to 20 mg, niacin 1 mg to 100 mg, and pantothenic acid 1 mg to 100 mg, wherein the composition includes no additional lipid, and the composition further comprises at least two of the following (i)-(iii):

(i) at least one selected from the group consisting of alpha lipoic acid, coenzyme Q10, and blueberry extract, (ii) at least one selected from magnesium, copper and chromium, and (iii) galacto-oligosaccharide.

11. The method according to claim 10, wherein the composition is administered orally or through a tube in a dose of one dosage unit per day.

12. The method according to claim 10, wherein the patient is with the disease selected from the group consisting of hypertension, dental caries, and periodontal disease.

13. A method of treating a patient with a life style-related disease that is irrespective of age and excludes hyperlipidemia, comprising administering to the patient an effective amount of a composition per dosage unit for reducing the levels of glucose, malondialdehyde-modified LDL, homocysteine, and C-reactive protein in the blood, the composition comprising:

(a) vitamin $B_{12}$ from 1.1 μg to 50.0 μg, vitamin $B_6$ from 1.6 mg to 60.0 mg, and folic acid from 200 μg to 1.1 mg;

(b) zinc from 1.2 mg to 30 mg, selenium from 10 μg to 250 μg vitamin C from 100 mg to 2000 mg, and vitamin E from 3 mg to 600 mg; and (c) vitamin $D_3$ from 1 μg to 10 μg, vitamin $B_1$ from 1.0 mg to 5.0 mg, biotin from 10 μg to 100 μg, vitamin $B_2$ from 0.5 mg to 20 mg, niacin 1 mg to 100 mg, and pantothenic acid 1 mg to 100 mg, wherein the composition includes no additional lipid, the vitamins in the composition consist of folic acid, biotin, niacin, pantothenic acid, and vitamins $B_1$, $B_2$, $B_6$, $B_{12}$, C, $D_3$, and E, and the composition further comprises at least two of the following (i)-(iii):

(i) at least one selected from the group consisting of alpha lipoic acid, coenzyme Q10, and blueberry extract, (ii) at least one selected from magnesium, copper and chromium, and (iii) galacto-oligosaccharide.

14. The method according to claim 13, wherein the composition is administered orally or through a tube in a dose of one dosage unit per day.

15. The method according to claim 13, wherein the patient is with the disease selected from the group consisting of hypertension, dental caries, and periodontal disease.

16. A method of treating a patient with a life style-related disease that is irrespective of age and excludes hyperlipidemia, comprising administering to the patient an effective amount of a composition per dosage unit for reducing the levels of glucose, malondialdehyde-modified LDL, homocysteine, and C-reactive protein in the blood, the composition comprising:

(a) vitamin $B_{12}$ from 1.1 μg to 50.0 μg, vitamin $B_6$ from 1.6 mg to 60.0 mg, and folic acid from 200 μg to 1.1 mg;

(b) zinc from 1.2 mg to 30 mg, selenium from 10 μg to 250 μg vitamin C from 100 mg to 2000 mg, and vitamin E from 3 mg to 600 mg;

(c) vitamin $D_3$ from 1 μg to 10 μg, vitamin $B_1$ from 1.0 mg to 5.0 mg, biotin from 10 μg to 100 μg, vitamin $B_2$ from 0.5 mg to 20 mg, niacin 1 mg to 100 mg, and pantothenic acid 1 mg to 100 mg, and the composition further comprises at least two of the following (i)-(iii):

(i) at least one selected from the group consisting of alpha lipoic acid, coenzyme Q10, and blueberry extract, (ii) at least one selected from magnesium, copper and chromium, and (iii) galacto-oligosaccharide wherein the composition includes no additional lipid.

17. The method according to claim 16, wherein the composition is administered orally or through a tube in a dose of one dosage unit per day.

18. The method according to claim 16, wherein the patient is with the disease selected from the group consisting of hypertension, dental caries, and periodontal disease.

19. A method of treating a patient with a life style-related disease that is irrespective of age and excludes hyperlipidemia, comprising administering to the patient an effective amount of a composition per dosage unit for reducing the levels of glucose, malondialdehyde-modified LDL, homocysteine, and C-reactive protein in the blood, the composition comprising:

(a) vitamin $B_{12}$ from 1.1 μg to 50.0 μg, vitamin $B_6$ from 1.6 mg to 60.0 mg, and folic acid from 200 μg to 1.1 mg;

(b) zinc from 1.2 mg to 30 mg, selenium from 10 μg to 250 μg vitamin C from 100 mg to 2000 mg, and vitamin E from 3 mg to 600 mg; and (c) vitamin $D_3$ from 1 μg to 10 μg, vitamin $B_1$ from 1.0 mg to 5.0 mg, biotin from 10 μg to 100 μg, vitamin $B_2$ from 0.5 mg to 20 mg, niacin 1 mg to 100 mg, and pantothenic acid 1 mg to 100 mg, wherein the composition includes no additional lipid, and the minerals in the composition consist of zinc and selenium, and the composition further comprises at least two of the following (i)-(iii):

(i) at least one selected from the group consisting of alpha lipoic acid, coenzyme Q10, and blueberry extract, (ii) at least one selected from magnesium, copper and chromium, and (iii) galacto-oligosaccharide.

20. The method according to claim 19, wherein the composition is administered orally or through a tube in a dose of one dosage unit per day.

21. The method according to claim 19, wherein the patient is with the disease selected from the group consisting of hypertension, dental caries, and periodontal disease.

* * * * *